US006740225B2

(12) United States Patent
Gurry et al.

(10) Patent No.: US 6,740,225 B2
(45) Date of Patent: May 25, 2004

(54) METHOD FOR DETERMINING THE AMOUNT OF CHLORINE AND BROMINE IN WATER

(75) Inventors: Bonnie Gurry, Solon, OH (US); Meijun Shao, Richmond Heights, OH (US); Laurie Dudik, South Euclid, OH (US); Chung-Chiun Liu, Cleveland Heights, OH (US)

(73) Assignee: Hathaway Brown School, Shaker Heights, OH (US)

( * ) Notice: Subject to any disclaimer, the term of this patent is extended or adjusted under 35 U.S.C. 154(b) by 268 days.

(21) Appl. No.: 09/799,969

(22) Filed: Mar. 6, 2001

(65) Prior Publication Data

US 2001/0042692 A1 Nov. 22, 2001

Related U.S. Application Data

(60) Provisional application No. 60/187,528, filed on Mar. 7, 2000.

(51) Int. Cl.[7] ........................ G01N 27/333; G01N 27/26
(52) U.S. Cl. ................................ 205/778.5; 205/779.5; 204/416; 204/431
(58) Field of Search ........................... 204/400, 416, 204/431; 205/778.5, 779, 779.5

(56) References Cited

U.S. PATENT DOCUMENTS

| 3,707,455 A | * 12/1972 | Derr et al. ............ 204/403.09 |
| 4,571,292 A | 2/1986 | Liu et al. |
| 4,655,880 A | 4/1987 | Liu |
| 4,865,717 A | 9/1989 | Setter et al. |
| 4,874,500 A | 10/1989 | Madou et al. |
| 5,000,180 A | 3/1991 | Kuypers et al. |
| 5,120,421 A | 6/1992 | Glass et al. |
| 5,336,388 A | 8/1994 | Leader et al. |
| 5,387,462 A | 2/1995 | Debe |
| 5,437,772 A | 8/1995 | De Castro et al. |
| 5,437,999 A | 8/1995 | Diebold et al. |
| 5,514,337 A | 5/1996 | Groger et al. |
| 5,676,820 A | 10/1997 | Wang et al. |
| 5,958,340 A | 9/1999 | Meyer et al. |

FOREIGN PATENT DOCUMENTS

| GB | 2290617 A | * 3/1996 |
| WO | 95/29400 | * 11/1995 |

OTHER PUBLICATIONS

Fraden, Jacob, "Chemical Sensors," AIP Handbook of Modern Sensors, American Institute of Physics (New York), pp. 532–546, 1993.

Ann Lai, et al. United States Ser. No. 09/466,865, (Dec. 17, 1999).

* cited by examiner

Primary Examiner—Alex Noguerola
(74) Attorney, Agent, or Firm—Renner, Kenner, Greive, Bobak, Taylor & Weber

(57) ABSTRACT

A thick film electrochemical microsensor device for measuring or regulating chlorine and bromine in water, comprising a substrate to which is applied an optimum arrangement of at least two electrodes. The device is especially useful for measuring or regulating chlorine and bromine levels in swimming pool or spa water. A method of measuring or regulating ions of at least one of chlorine and bromine in water is also described, which comprises contacting the water with the microsensor of the present invention; measuring the current output of the microsensor; determining the level of at least one of chlorine and bromine indicated by the current output; and generating a signal.

12 Claims, 3 Drawing Sheets

METHOD FOR DETERMINING THE AMOUNT OF CHLORINE AND BROMINE IN WATER

CROSS REFERENCE TO RELATED APPLICATIONS

This application claims priority from U.S. Provisional Application No. 60/187,528, filed on Mar. 7, 2000.

TECHNICAL FIELD

The present invention is directed to a microsensor device for measuring or regulating at least one of chlorine and bromine ions. More particularly, the invention is directed to a thick film electrochemical microsensor capable of measuring or regulating the level of chlorine and bromine ions in swimming pool or spa water. The invention further encompasses a method of measuring or regulating the levels of chlorine and bromine ions in swimming pool or spa water using the electrochemical microsensor.

BACKGROUND OF THE INVENTION

In order to insure that the water in a pool or spa is safe, it must be properly sanitized to prevent any health problems arising due to algae, bacteria, or any other pathogens which may be in the water. Currently, chlorine and bromine are commonly used to sanitize pools or spas. The chlorine comes in a number of different forms: sodium hypochlorite (liquid bleach), calcium hypochlorite, lithium hypochlorite or chlorinated isocyanurates. When any of these materials interact with water, they undergo hydrolysis to form free chlorine consisting of predominantly hypochlorous acid (HOCl), which is the sanitizing agent, and hypochlorite ion. Free available chlorine (FAC) is the amount of unused or unreacted chlorine. Combined available chlorine (CAC), also known as chloramines, is the portion of chlorine which has interacted and combined with contaminants. For the purposes of this invention, measurement of chlorine refers to the chlorine ion $Cl^{-1}$, as well as hypochlorous acid HOCl, and hypochlorite ion $OCl^{-1}$.

The National Spa and Pool Institute recommends 1 to 3 parts per million of free chlorine in the water and a pH between 8 and 10. Most pool or spa owners use a visual test which measures the amount of total chlorine in the water, not the amount of free available chlorine. This visual test can be incorrectly performed or inaccurately interpreted, and the wrong amount of chlorine may then be added to the water. This inaccuracy often leads to an unwanted chlorine odor, red, burning eyes, or the spread of diseases among the swimmers.

Electrochemical sensors have been used in various fields because of their cost effective mode of operation and uncomplicated method of manufacture. U.S. Pat. No. 5,676,820 to Wang et al. describes a sensor used to monitor metal contaminants in a remote location, connected via a communications cable to an analysis device. Microsensors have also been used to detect acidity in water, as well as to monitor species such as carbon dioxide and hydrogen sulfide.

It is therefore an object of the present invention to provide a thick film electrochemical microsensor for measuring or regulating at least one of chlorine and bromine in water such as swimming pool and spa water.

SUMMARY OF THE INVENTION

The present invention provides an electrochemical microsensor device for measuring or regulating ions of at least one of chlorine and bromine comprising, a substrate supporting an arrangement of at least two electrodes, wherein one of the electrodes is an anode and one of the electrodes is a cathode, wherein the electrodes are formed or fabricated using a thick film technique, and wherein the anode is adapted for oxidation of chlorine and bromine ions.

The present invention further provides a method of measuring or regulating ions of at least one of chlorine and bromine in water comprising contacting the water with the electrochemical microsensor device of the invention, measuring the current output of the sensor, determining the level of chlorine and bromine indicated by the current output, and generating a signal.

It has been found that chlorine and bromine can be measured in water using a thick film electrochemical microsensor device. Novel electrode configurations were designed and tested, and the results are reported herein, along with a preferred electrode configuration.

Advantageously, the thick film electrochemical microsensor device of the present invention can be used to actuate a regulating means to maintain an appropriate level of chlorine and/or bromine in swimming pool or spa water.

DETAILED DESCRIPTION OF THE INVENTION

Figure 1:
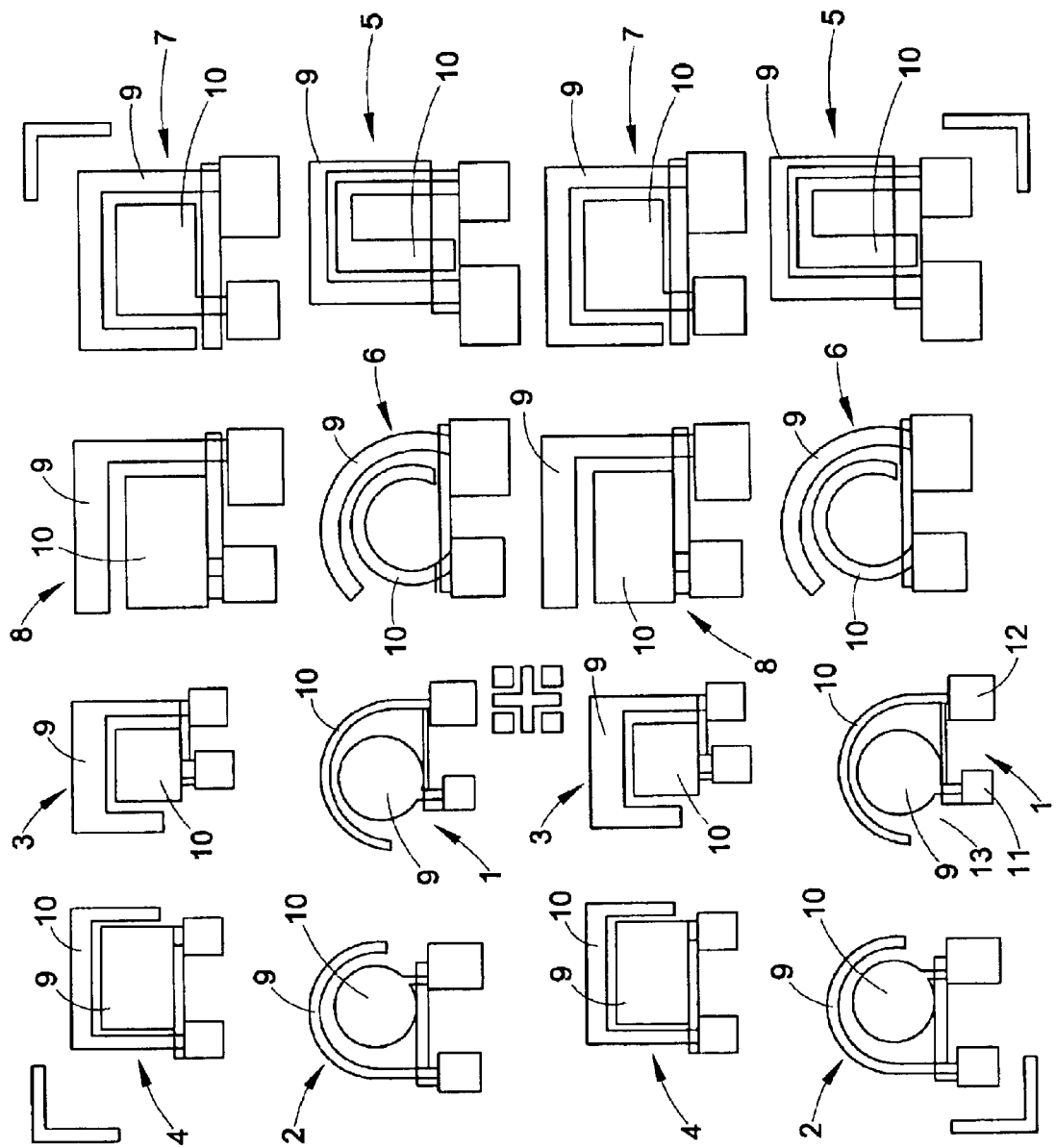
FIG. 1 is a schematic illustration of the design of 8 thick film electrochemical microsensors prepared and tested in accordance with the invention.

The present invention is directed to a thick film electrochemical sensor device that is capable of being used to measure or regulate chlorine and bromine ion levels in water such as swimming pool or spa water.

More specifically, the present invention is directed to the fabrication and use of a chip-like thick film electrochemical microsensor device with at least two electrodes, including an anode and a cathode, arranged on an inert substrate. The overall size of the microsensor device can vary greatly, dependent only on economic efficiency and user preference.

The microsensor device of the present invention is an electrochemical system in which a reversible redox reaction takes place. Electrochemical methods of analysis include all methods of analysis that measure current, potential and resistance, and relate them to analyte concentration. Voltammetric techniques have been classified as dynamic electrochemical techniques. In their operation the potential is controlled and the current is monitored. Voltammetric techniques are based on the measurement of current as a function of potential. The current is produced at an electrode surface following the oxidation or reduction of the analyte at a characteristic potential. Oxidation or reduction at the electrode surface is essentially electron-transfer (or charge transfer). In any voltammetric technique it is the charge transfer that is being measured. The current is measured in amperes i.e. the rate of flow of charge. Voltammetric measurements are therefore measurements of the rate of reaction. The electrochemical reaction at the electrode surface is driven by the application of a potential to that electrode. The applied potential is the excitation signal and the measured current is the resulting signal. The potential at which the reaction occurs is characteristic of the analyte, based on the Gibbs free energy for the reaction, and the amount of current that is measured is related to concentration.

The sensor is preferably made using a thick film technique, including deposition of multiple electrodes on a substrate. Electrochemical sensors and thick film techniques for their fabrication are discussed in U.S. Pat. No. 4,571,292 to C. C. Liu et al, U.S. Pat. No. 4,655,880 to C. C. Liu, and co-pending application U.S. Ser. No. 09/466,865 to Lai et al, which patents and application are incorporated by reference as if fully written out below.

The substrate may be formed of plastic, glass, ceramic, alumina, quartz, or any other material that preferably is inert relative to the material from which the electrodes are formed and the material into which the sensor is intended to be placed for use. Preferably the substrate is an alumina ceramic material. Other suitable ceramics include aluminum nitride, silicon carbide, silicon nitride, and the like.

The multiple electrodes include at least one each of an anode and a cathode. The anode is the working electrode, and should preferably be composed of a material that is inert relative to the substrate and the chlorine and bromine. The working electrode functions, via oxidation of chlorine and bromine ions, to draw current flow detectable by known measuring means. Examples of materials suitable for the anode include, but are not limited to, gold, platinum, palladium, silver, and carbon. Preferred materials are platinum or gold. Platinum, for example, is applied to the substrate in the form of a platinum ink, which is commercially available, or can be made using finely dispersed metal particles, solvent, and a binder. Ultra violet (UV)-cured platinum ink is commercially available, and can also be used in forming the electrodes.

Specific examples of suitable materials to form the cathode are silver-silver chloride and mercury-mercuric chloride (Calomel). Silver-silver chloride is preferred. The silver is applied to the substrate in the form of a silver ink, which is commercially available, or can be made using finely dispersed metal particles, solvent, and a binder. Ultra violet (UV)-cured silver ink is commercially available, and can also be used in forming the electrode. As described in further detail herein, the silver is exposed to chloride solution to produce the silver-silver chloride electrode.

The electrodes of the sensor apparatus of the present invention may include a connect portion and a sensing portion. The sensing portion of the electrode is exposed to the environment, and is in contact with the electrolyte and the target species. The sensing portion functions to detect the target species as discussed above. The connect portion of the electrode connects the electrode to an electrical circuit, and is protected from the environment by an insulator. The insulator used to protect the connect portion of the electrodes of the present invention is preferably glass, and is applied in the form of an insulating ink. In a preferred embodiment, wires are soldered to the connect portion of the electrodes using indium solder. The wires and the solder are then covered with a silicone paste.

The arrangement of the electrodes on the substrate is important. The cathode (reference electrode) is placed close to the anode (working electrode). The shapes of the electrodes are important, as is their size or any modification to their surfaces.

According to the invention, sensor designs were drawn on AUTO-CAD™, a computer drafting program. Then, through a thick film process, which is similar to the silk screening process, silver, platinum, and insulating precursor inks were printed onto alumina ceramic substrates to form the electrodes. The silver was treated with chloride to form silver-silver chloride, the material used for the cathode, and platinum was used for the anode. The microsensors were heated to solidify the components, the wires were soldered to the contacts, and silicone paste was applied and cured. Finally, the sensors were tested by exposure to chlorine and bromine concentrations of from about 0 to about 2.0%.

To use the microsensor device, a voltage must be applied and the current measured. The voltage used depends on the target species and the type of electrodes. The corresponding current produced is measured and used to quantify the concentration of the target species, namely chlorine and bromine ions.

Specific Embodiments of the Invention

The sensor configurations fabricated and tested according to the invention are shown in FIG. 1. Sensor examples nos. 1–8 are numbered accordingly. Sensor example no. 1 comprises an anode 9, a cathode 10, and contacts 11, 12, where connecting wires are attached, arranged on a substrate 13. As shown in FIG. 1, each sensor configuration comprises an anode 9, and a cathode 10, with differences in shape, size, and placement on the substrate.

Figure 2:
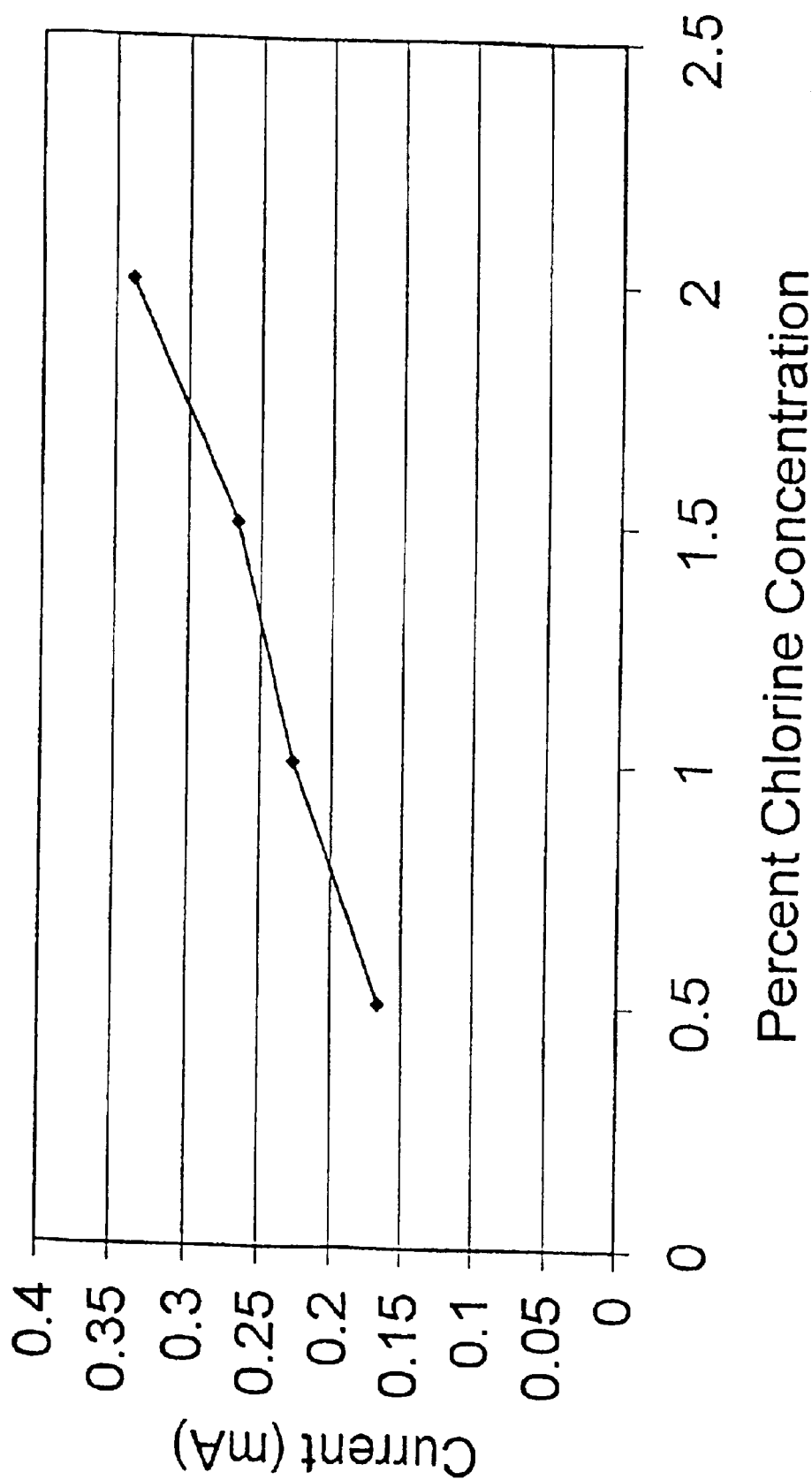
FIG. 2 is a graphical representation of the current output for the sensor of example no. 1 in relation to chlorine ion concentrations from 0.0 to 2.0%.

Results of tests done on sensor example no. 1 are shown in FIG. 2. The current output is plotted versus the concentration of chlorine in the test solutions, which ranges from 0 to 2.0 percent. The data shown in FIG. 2 was measured at 0.5 V.

Figure 3:
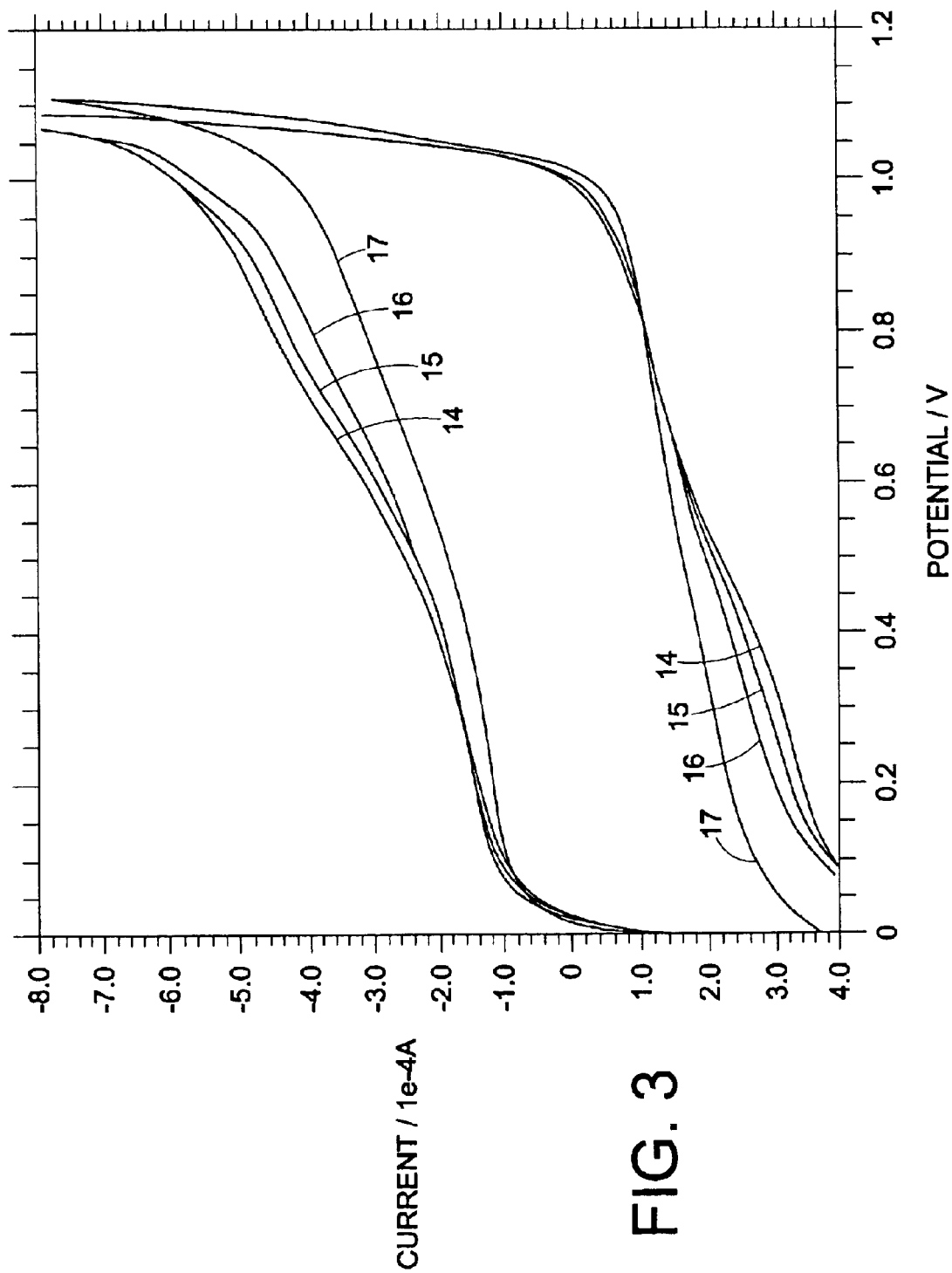
FIG. 3 is a graphical representation of the current output for the sensor of example no. 4 over a range of voltages from 0 to 1.2 V.

Results of tests done on sensor example no. 4 are shown in FIG. 3. The current output is plotted versus the applied potential, which was varied over a range of 0 to 1.0 V. Line nos. 14 to 17 correspond to test solutions of 0.5, 1.0, 1.5, and 2.0% chlorine ions, respectively.

Experimental Procedures

The thick film microsensors according to the invention were fabricated according to the procedure below.

Eight designs were developed and drawn using an AUTO-CAD™ program. They were then converted into screen patterns by one of the following methods. 1.) The designs were magnified ten times and read into a program called SHADI, which directed the RUBYLITH™ cutter to cut the designs onto a plastic RUBYLITH™ material. The outer coating of the RUBYLITH™ was peeled away from the interior of the design, leaving the design clear. This design was then placed over a light source and a photographic plate was exposed leaving the design black when developed. 2.) The interior of the eight designs were filled in black using the AUTO-CAD™ program. The designs were printed out onto transparencies, which were then cut into four by four inch squares.

The resulting pattern was placed onto a sheet of photosensitive plastic. The plastic was placed under ultraviolet light, exposing the plastic where there was no design. The unexposed portions were removed, and the plastic was attached to a metal screen. The metal screen was placed into a metal frame to form a template. A separate template was prepared for each electrode and for the insulator ink.

The templates were then used with a thick film printer to "silk screen" the patterns onto a ceramic substrate. A template was contacted with the substrate, and placed into the printer. The printer first applied the platinum precursor ink onto the substrate, according to the pattern of the template. Next, the silver was applied. Finally, the insulator ink was applied. Transferring the pattern from the template to the substrate in this manner forms a sensor configuration on the substrate.

After the precursor inks had been applied, the substrate was placed in a drying oven at about 100° C., and then fired in a furnace at about 850° C. to cure the electrode precursors and solidify the sensor device.

Afterwards, the substrates were diced using a diamond saw into individual devices. The resulting sensor devices were approximately 0.75 inches wide by 0.75 inches long. The wires were soldered to the connect portion of the sensor device using a soldering iron, flux, and indium solder. The connect portion of the sensor device was then covered with insulation, such as silicone. The silver electrode of the sensor device was cleaned using a mechanical pencil eraser. 0.1M hydrochloric acid solution was placed in a beaker. A platinum screen was connected to the negative (cathodic) side of a potentiostat. The wire attached to the silver electrode was connected to the positive (anodic) side of the potentiostat. Both the platinum screen and the sensor device were placed into the beaker of 0.1M hydrochloric acid without allowing them to touch one another. A voltage of 0.5V was applied. The silver surface was first cleaned by turning the power up for 5 seconds and down for 5 seconds three times. Then the chloride was allowed to react with the silver to form silver-silver-chloride by leaving the power on for 2 minutes. The sensor was rinsed using warm water and de-ionized water, and placed on paper towels to dry.

Testing was done using solutions containing concentrations of chlorine in the amount of 0.5, 1.0, 1.5, and 2.0 percent. The sensor to be tested was connected to a potentiostat. The silver-silver chloride electrode was connected to the negative (cathodic) side of the potentiostat, and the platinum (working) electrode was connected to the positive (anodic) side of the potentiostat. A voltage was applied from between 0 to about 1.1 V. The current required to effect the oxidation of chlorine ions to chlorine atoms was measured for each solution. Calculations were made relating current output to concentration of chlorine in the solution, and to voltage. Typical results are shown in FIGS. 2 and 3, respectively. A summary of regression factors R for each of the sensor examples 1–8 for the plot of current versus chlorine concentration at 0.5 V is shown in Table 1. As can be seen from the data in Table 1. microsensor example no. 1 appears to show the best correlation between chlorine concentration and current output. This was also evident at other voltages tested.

TABLE 1

R Values at 0.5 V for Plot of Current versus Chlorine Concentration

| Sensor Example No. | R Value |
|---|---|
| 1 | 0.994270 |
| 2 | 0.817087 |
| 3 | 0.766172 |
| 4 | 0.495908* |
| 5 | 0.849220 |
| 6 | 0.517890 |
| 7 | 0.783139 |
| 8 | 0.703463 |

*R value calculated for data measured at 0.6 V.

Further testing was done, as described above, using concentrations of bromine in the amount of 0.5, 1.0, 1.5 and 2.0 percent. In addition, mixed solutions containing both chlorine and bromine were tested. Results are summarized in Table 2. As can be seen from the data in Table 2, microsensor examples 1 and 5 gave the best results.

TABLE 2

| Sensor No. | 1 | 2 | 3 | 4 | 5 | 6 | 7 | 8 |
|---|---|---|---|---|---|---|---|---|
| Solution | Br | Br | Br | Br | Br | Br | Br | Br |
| Best R²-Value | .9627 | .8959 | .9524 | .9346 | 1 | .5768 | .2076 | .7798 |
| Voltage | 1.0 | 1.0 | 1.0 | 1.0 | .5 | 1.0 | .9 | .8 |
| Solution | X % Cl and 1% Br | X % Cl and 1% Br | X % Cl and 1% Br | X % Cl and 1% Br | X % Cl and 1% Br | X % Cl and 1% Br | X % Cl and 1% Br | X % Cl and 1% Br |
| Best R-Value | .9206 | .8389 | .9602 | .8890 | .9581 | .4382 | .9936 | .7065 |
| Voltage | 1.1 | 0.4 | 0.1 | 1.1 | 1.0 | 0.7 | 0.7 | 1.0 |
| Solution | 1% Cl and X % Br | 1% Cl and X % Br | 1% Cl and X % Br | 1% Cl and X % Br | 1% Cl and X % Br | 1% Cl and X % Br | 1% Cl and X % Br | 1% Cl and X % Br |
| Best R-Value | .9824 | .9686 | .9925 | .9589 | — | .9996 | .9681 | .6538 |
| Voltage | 1.1 | 0.15 | 0.2 | 0.15 | — | 1.1 | 0.1 | 0.9 |

Solutions containing lower levels of chlorine and bromine were also tested using microsensors 1 and 5. Test solutions were prepared to contain 25, 50, 75 and 100 parts per million chlorine or bromine. Results are summarized in Table 3.

TABLE 3

| Sensor No. | 5 | 1 | 5 |
|---|---|---|---|
| Solution | Cl | Br | Br |
| Best R-Value | .9962 | .9546 | .9871 |
| Voltage | .7 | .7 | .7 |

Sensor example no. 1 provided the best correlation between current output and chlorine concentration. Sensitivity was good even at low voltages of around 0.3 V. The electrode configuration for sensor example no. 1 comprises a rounded anode disposed within the cathode which has a concentric arm design. Another preferred embodiment, sensor example no. 5, gave reasonably good results. The electrode configuration for sensor example no. 5 comprises a cathode that is a square arm disposed within and surrounded on three sides by a similarly shaped anode.

Advantageously, the microsensor device of the present invention, prepared using a thick film technique, is relatively inexpensive to manufacture, install, and operate. For this reason, it is possible to use dual sensors and operate them in a differential mode. In a preferred embodiment, two substantially identical sensors are used. One sensor is optimized for chlorine and bromine detection, and the second sensor is adapted to detect interference from other chemical species, through the use of an electrode catalyst or other means. The levels of chlorine and bromine can then be determined by subtracting the signal due to the interference from the signal of the chlorine and bromine detecting sensor. Such a method of differential operation can overcome the problems of interference that are known in the art of electrochemical sensors.

The method of this embodiment comprises contacting the water with a first inventive sensor adapted to detect chlorine and bromine, measuring the current output of the sensor, generating a first signal based on the current output of the sensor, providing a second inventive sensor, which has been adapted to detect interferences from other chemical species, contacting the water with the second sensor, measuring the current output of the second sensor, generating a second signal, and subtracting the second signal from the first signal. This signal can then be used to activate a display device, a recording means, an alarm device, and/or a regulating means.

It is demonstrated that the electrochemical microsensor device of the present invention can be used to measure chlorine and bromine cheaply and quite effectively in various locations, including swimming pools and spas. When chlorine and bromine levels are determined, the sensor generates a signal that is sent to an indicator, such as an alarm, or visual display, or to a recorder, making it possible to study trends and track chlorine and bromine levels over a period of time. Current flow can be measured by a potentiostat, for example, or analyzed by computer or another electronic measuring device. The sensor can generate a visual or audible alarm signal when the concentration of chlorine ions is determined to be outside a predetermined range. Additionally, the sensor can generate a signal that is amplified if necessary, and that triggers an actuator, to activate a regulating means, such as an existing chlorine dispenser, only when pre-determined levels of chlorine and bromine are measured, or to inactivate the chlorine or bromine dispenser, allowing more efficient utilization of the dispensing system.

It should now be apparent that various embodiments of the present invention accomplish the object of this invention. It should be appreciated that the present invention is not limited to the specific embodiments described above, but includes variations, modifications, and equivalent embodiments defined by the following claims.

What is claimed is:

1. A method of measuring or regulating ions of at least one of chlorine and bromine in water comprising:

contacting the water with a first electrochemical microsensor device comprising, a substrate supporting an arrangement of at least two electrodes, wherein one of the electrodes is an anode and one of the electrodes is a cathode, wherein the electrodes are formed using a thick film technique wherein the anode and the cathode are disposed adjacent to each other, and one said electrode is substantially nested within the other said electrode substantially within the same plane, and wherein the anode is adapted for oxidation of ions of said at least one of chlorine and bromine;

measuring the current output of the first microsensor;

determining the level of said at least one of chlorine and bromine indicated by the current output; and generating a signal.

2. The method of claim 1, further comprising transmitting the signal to at least one device selected from the group consisting of display devices, recording means, alarm devices, and regulating means.

3. The method of claim 2, wherein the regulating means comprises a chlorine or bromine dispensing means.

4. The method of claim 1, wherein said step of determining the level of said at least one of chlorine and bromine indicated by the current output comprises:

generating a first signal based on the current output of the first microsensor;

providing a second microsensor substantially identical to the first microsensor, wherein the second microsensor is adapted to detect interference from chemical species other than chlorine and bromine;

contacting the water with the second microsensor;

measuring the current output of the second microsensor;

generating a second signal based on the current output of the second microsensor; and subtracting the second signal from the first signal.

5. The method of claim 1 wherein the substrate is an insulating material selected from the group consisting of plastic, glass, ceramic, quartz, and mixtures thereof.

6. The method of claim 1, wherein the substrate is alumina.

7. The method of claim 1, wherein the anode comprises a material selected from the group consisting of gold, platinum, palladium, silver, and carbon.

8. The method of claim 1, wherein the cathode comprises a material selected from the group consisting of silver-silver chloride and mercury-mercuric chloride.

9. The method of claim 1, wherein said electrodes each comprises a connect portion and a sensing portion, wherein said connect portion of each electrodes connects the electrode to an electrical circuit, and is protected from the environment by an insulator, and wherein said sensing portion of each electrode is exposed to the environment.

10. The method of claim 1, wherein the thick film technique comprises:

providing at least one template containing a pattern for the arrangement of the electrodes;

contacting the substrate with the template;

applying at least one electrode precursor ink, and insulator precursor ink onto the template/substrate to form a sensor configuration according to the template pattern;

drying the sensor configuration; and firing the sensor configuration.

11. The method of claim 1, wherein a first of said electrodes is rounded and a second of said electrodes has a concentric arm design, and wherein the first said electrode is disposed within the concentric arm of the second said electrode.

12. The method of claim 1, wherein a first of said electrodes and a second of said electrodes each have a square arm shape and the first said electrode is disposed within and surrounded on three sides by the second said electrode.

* * * * *